(12) United States Patent  (10) Patent No.: US 8,977,337 B2
Oyama                      (45) Date of Patent:     Mar. 10, 2015

(54) PHOTOACOUSTIC DIAGNOSTIC APPARATUS

(75) Inventor: Kenji Oyama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 120 days.

(21) Appl. No.: 13/810,756

(22) PCT Filed: Jul. 8, 2011

(86) PCT No.: PCT/JP2011/003921
§ 371 (c)(1),
(2), (4) Date: Jan. 17, 2013

(87) PCT Pub. No.: WO2012/014390
PCT Pub. Date: Feb. 2, 2012

(65) Prior Publication Data
US 2013/0123604 A1    May 16, 2013

(30) Foreign Application Priority Data

Jul. 28, 2010 (JP) .................... 2010-169299

(51) Int. Cl.
*A61B 5/00* (2006.01)
(52) U.S. Cl.
CPC ............ *A61B 5/0095* (2013.01); *A61B 5/7221* (2013.01); *A61B 5/4312* (2013.01); *A61B 5/708* (2013.01)

USPC ........................................................ 600/407
(58) Field of Classification Search
CPC .... A61B 5/0095; A61B 5/708; A61B 5/4312; A61B 5/7221
See application file for complete search history.

(56) References Cited

U.S. PATENT DOCUMENTS

| 5,713,356 A | 2/1998 | Kruger .................. 128/653.1 |
| 2013/0205903 A1 | 8/2013 | Oyama ........................ 73/596 |

FOREIGN PATENT DOCUMENTS

JP      09-145683      6/1997

*Primary Examiner* — Long V Le
*Assistant Examiner* — Colin T Sakamoto
(74) *Attorney, Agent, or Firm* — Fitzpatrick, Cella, Harper & Scinto

(57) ABSTRACT

A photoacoustic diagnostic apparatus having a light source, a probe which receives an acoustic wave generated when light is directed onto an object from a light source and which converts the acoustic wave into an electrical signal, a memory unit which records the electrical signal and a memory control unit which controls whether or not to cause the memory unit to record the electrical signal. The memory control unit controls the memory unit on the basis of a timing at which the probe receives an acoustic wave generated from a portion other than a light absorbing material inside an object.

7 Claims, 11 Drawing Sheets

PHOTOACOUSTIC DIAGNOSTIC APPARATUS

TECHNICAL FIELD

The present invention relates to a photoacoustic diagnostic apparatus.

BACKGROUND ART

Thus far, a large number of proposals have been made in relation to technology for capturing diagnostic images using light, and one of these proposals is photoacoustic tomography (called PAT below). An apparatus using PAT is particularly useful in diagnosis of skin cancer or breast cancer, and there are high expectations for the use of this kind of apparatus as a medical device in place of an ultrasound diagnostic apparatus, an X-ray apparatus, or an MRI apparatus, which have been used conventionally for such diagnosis.

The basic measurement principle of PAT is based on that of photoacoustic analysis technology, such as that disclosed in Patent Literature 1 (see below). According to the technology disclosed in Patent Literature 1, measurement light produced by a light source is directed onto a specimen via an irradiation optical system, and a photoacoustic wave from the specimen is received by one ultrasound probe, whereby it is possible to measure photoacoustic characteristics of the specimen.

If measurement light, such as visible light or near-infrared light, or the like, is irradiated onto living tissue, a light absorbing material inside the living organism, and in particular, material such as hemoglobin in the blood, and the like, absorbs energy from the measurement light and generates a photoacoustic wave as a result of this. In PAT, information about the living tissue is visualized by measuring this photoacoustic wave. With PAT technology, it is possible to achieve quantitative measurement, and also three-dimensional measurement, of the density distribution of light energy absorption, in other words, the density distribution of light absorbing material, in the living organism.

Moreover, by combination with ultrasound diagnostic technology using ultrasound echo, it is possible simultaneously to measure distribution information about internal tissue of a living organism based on a photoacoustic analysis method, and information about the morphological characteristics of the internal tissue of the living organism by ultrasound diagnostic technology, which is suitable for accurate diagnosis through more precise characterization of diagnostic results.

In general, in the diagnosis of breast cancer, an overall pass/fail diagnosis is made on the basis of the results of palpation or the plurality of modalities described above. The key bases for this diagnosis are image diagnostic results which indicate the presence or absence of new blood vessels, which are produced by cancer. A photoacoustic image obtained in relation to breast cancer which has an increased blood flow compared to normal tissue, due to the new blood vessels, has the potential for providing superior detection capability compared to measurement by a conventional ultrasound diagnostic apparatus or an X-ray apparatus or MRI apparatus, or the like.

Moreover, PAT has a significant benefit in terms of the burden on the patient, since light is used for capturing a diagnostic image and therefore image diagnosis by radiation-free, non-invasive means is possible, and so may offer advances in screening and early diagnosis of breast cancer, compared to an X-ray apparatus, which cannot readily be used for repeated diagnosis, due to problems of radiation exposure.

With PAT which measures a photoacoustic wave produced as a result of a light absorbing material absorbing energy from measurement light, it is necessary to control the recording of the photoacoustic signal in synchronism with the irradiation of the tissue with the measurement light. In a solid-state laser, which is generally used as a light source, time lag (no more than 1 microsecond) and fluctuation (several tens of nsec approximately) occur from the input of a laser emission control signal until the actual emission of laser light, and therefore a method for achieving synchronism by detecting the measurement light is generally employed. To detect the measurement light, an optical composition is required which divides off a portion of the measurement light and guides the divided light portion to an optical sensor. Furthermore, the optical sensor used is required to have high-speed response which enables the measurement light to be measured as a pulse.

CITATION LIST

Patent Literature

[PTL 1]
Japanese Patent Application Publication No. H09-145683

SUMMARY OF INVENTION

Technical Problem

However, in the conventional technology described above, it has not been possible to solve the problems described below.

As stated above, an optical composition is required in order to detect the irradiation timing of the measurement light. However, providing an optical composition causes the apparatus to become larger in size. Furthermore, a portion of the measurement light must be divided off and measured, and this gives rise to a decline in the use efficiency of the measurement light. Consequently, there is a problem in that it is sought to remove the optical composition as far as possible.

More specifically, in a photoacoustic diagnostic apparatus, it is necessary to create means for detecting the irradiation timing of the measurement light in order to control recording of the photoacoustic wave signal, but with conventional technology, it has not been possible to address issues of cost and light use efficiency. If the optical composition for detecting the irradiation timing of the measurement light is to be omitted, this omission must not give rise to deterioration in the measurement accuracy or deterioration in the image quality of the photoacoustic diagnostic images, so that the accuracy of photoacoustic diagnosis is not impaired.

The present invention relates to the problems described above, an object thereof being to provide technology for omitting an optical composition for detecting the irradiation timing of measurement light, while maintaining desirable measurement accuracy and image quality, in measurement using PAT.

Solution to Problem

This invention provides a photoacoustic diagnostic apparatus, comprising a light source, a probe which receives an acoustic wave generated when light is directed onto an object from the light source and which converts the acoustic wave into an electrical signal, a memory unit which records the electrical signal, and a unit which controls whether or not to cause the memory unit to record the electrical signal. In this aspect the control unit controls the memory unit on the basis of a timing at which the probe receives an acoustic wave generated from a portion other than a portion of interest inside the object.

Advantageous Effects of Invention

According to the present invention, in measurement by PAT, it is possible to omit an optical composition for detecting the irradiation timing of measurement light, while maintaining desirable measurement accuracy and image quality.

Further features of the present invention will become apparent from the following description of exemplary embodiments with reference to the attached drawings.

DESCRIPTION OF EMBODIMENTS

A desirable mode for carrying out the present invention is described below with reference to the drawings. The dimensions, materials, shapes and relative positions, and the like, of the constituent parts described below should be changed appropriately depending on the composition and various conditions of the apparatus to which the invention is applied, and it is not intended to limit the scope of the invention to the description given below.

First Embodiment

A first embodiment of the present invention is now described with reference to the drawings.

Figure 1:
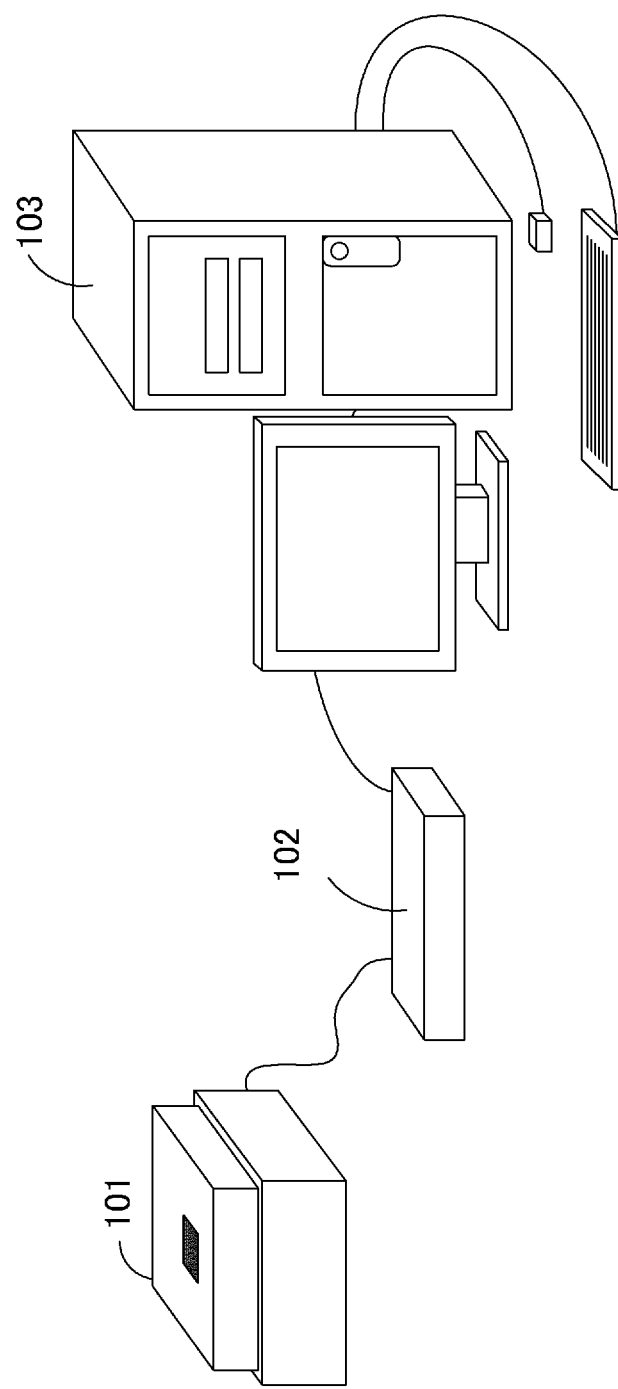
FIG. 1 is a schematic drawing of a photoacoustic diagnostic apparatus according to a first embodiment of the present invention.

FIG. 1 is a general diagram of the composition of a photoacoustic diagnostic apparatus using PAT according to a first embodiment of the invention.

The photoacoustic diagnostic apparatus in the present embodiment is constituted by a PAT 101, a PAT controller 102, and an image processing unit 103. PAT stands for "Photo Acoustic Tomography", and an apparatus using PAT technology is also referred to as "PAT" in the description given below.

The PAT 101 comprises irradiation means for irradiating measurement light onto an object, measurement means which measures a photoacoustic wave generated inside an object, and output means which outputs photoacoustic data to the image processing unit 103. Furthermore, the PAT 101 has a function of communicating with a controller 102, and exchanges commands and responses relating to the start of imaging, data transfer, and the like, with the controller 102.

The PAT 101 is a photoacoustic mammography apparatus having a head type composition for diagnosis in a prone position, which carries out diagnosis by inserting and holding a breast, which is the object of examination or inspection in this example, into a holding section of the apparatus. The application of the present invention is not limited to carrying out diagnosis with the patient in a prone position, and apart from this, it is also possible to carry out diagnosis with the patient in a standing position or a sitting position.

An image processing unit 103 connected to the controller 102 comprises image constructing means which generates a photoacoustic diagnostic image on the basis of photoacoustic wave data input from the PAT 101, and performs various corrections appropriate for diagnosis, and display means which displays a photoacoustic diagnostic image. The image processing unit 103 operates the PAT 101 via the controller 102. Upon receiving a measurement start command from the image processing unit 103, the PAT 101 measures the photoacoustic information of the interior of the object by the irradiation means and measurement means.

The controller 102 comprises functions for control processing of the measurement light source, integration processing in order to reduce noise in the measured photoacoustic wave, scanning control processing for controlling the measurement position, recording control processing for the photoacoustic wave signal which is characteristic of the present invention, transmission format conversion, and the like.

In FIG. 1, the image processing unit 103 and the controller 102 are provided as separate hardware, but it is also possible to provide a dedicated image processing unit which integrates the functions of both the controller 102 and the image processing unit 103. Furthermore, in FIG. 1, the PAT 101 and the controller 102 are provided as separate hardware, but it is also possible to provide all or a portion of the functions of the PAT 101 and the controller 102 in an integrated fashion. In the description given below, from a functional viewpoint, the PAT is described as a unit which combines the respective functions of the PAT 101 and the controller 102.

Furthermore, in the drawings, the respective apparatuses are connected by wires, but it is also possible to connect all or a portion of these apparatuses by wireless connections.

Figure 2:
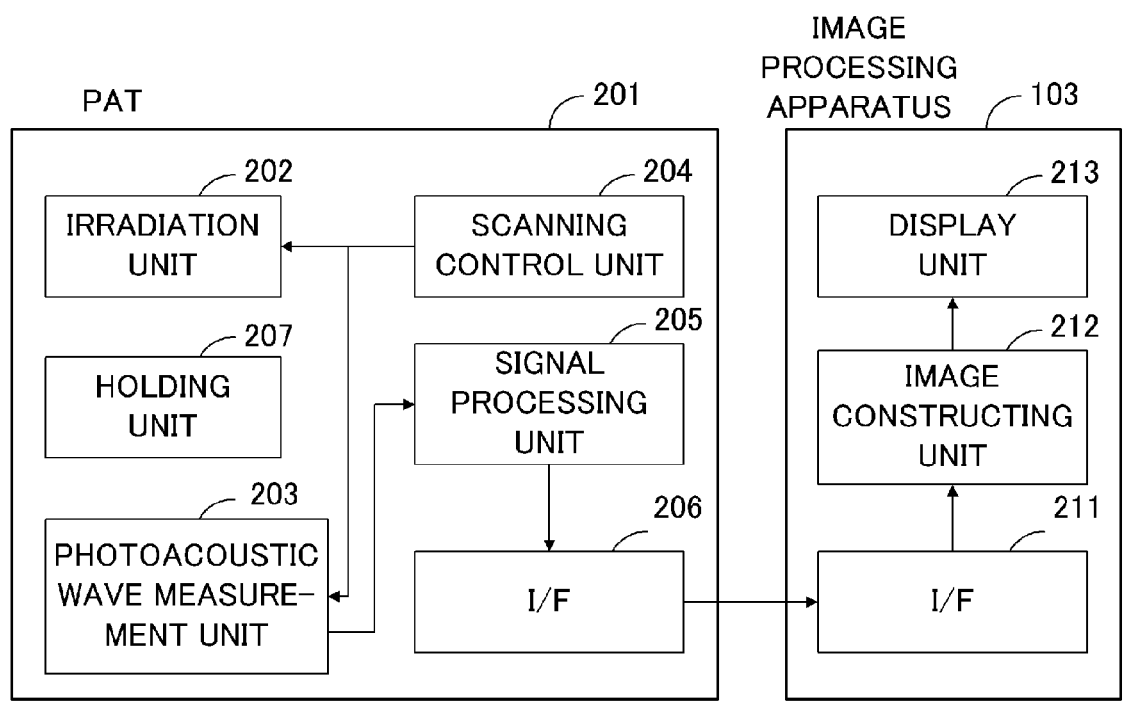
FIG. 2 is a functional block diagram of a PAT according to the first embodiment.

FIG. 2 is a functional block diagram of a PAT system in a first embodiment which describes the characteristics of the present invention. The PAT system comprises a PAT 201 and an image processing unit 103.

The PAT 201 is an apparatus having a scanning function capable of two-dimensionally controlling the measurement position of the acoustic wave. The PAT 201 comprises an irradiation unit 202 which irradiates measurement light, a photoacoustic wave measurement unit 203 which is characteristic of the present invention, and a scanning control unit 204 which two-dimensionally controls the measurement position. Moreover, the PAT 201 comprises a holding section 207 which holds an object, a signal processing unit 205 which carries out integration processing of the measured photoacoustic wave signal, and the like, and an interface (I/F) 206 with the image processing unit 103 which is an external processing unit.

The image processing unit 103 is an apparatus for generating and displaying photoacoustic diagnostic image data on the basis of photoacoustic data received from the PAT 201. The image processing unit 103 is constituted by an interface (I/F) 211 with the PAT 201, an image constructing unit 212 which generates acoustic diagnostic image data, and a display unit 213 which displays photoacoustic diagnostic images. In general, an apparatus such as a personal computer, workstation, or the like, having a high-performance calculation processing function and a graphic display function, is used for the image processing unit. In the case of a PAT system which is a medical device, the image processing unit also comprises a function for holding diagnostic information, such as photoacoustic diagnostic data or object identification information, or the like, and for sharing this diagnostic information via a network.

Firstly, the constituent elements of the PAT 201 will be described.

The irradiation unit 202 directs pulse-shaped laser light (having a pulse width of approximately 10 nsec) of visible light or near-infrared light, which is used as the measurement light, onto an object. The irradiation unit 202 is composed by a laser light source emitting pulse light and an irradiation optical system which guides measurement light to the object (the details of the irradiation unit 202 are described below with reference to FIG. 3). In the case of a construction which shines measurement light from both sides of an object by using two light sources, then light emission by the two light sources is controlled synchronously. The light source used for the measurement light is a solid-state laser (for example, an Yttrium-Aluminum-Garnet laser or Titan-Sapphire laser) capable of pulse light emission, which generally has a central wavelength in the near-infrared region. The wavelength of the measurement light is set between 530 nm and 1300 nm, in accordance with the light absorbing material inside the living organism (for example, hemoglobin, glucose, cholesterol, or the like) which is the object of measurement.

The hemoglobin in new vessels produced by breast cancer (when that is the measurement object) generally absorbs light having a wavelength of 600 to 1000 nm. On the other hand, light absorption by the water naturally present in the living organism is a minimum in the vicinity of 830 nm, so the difference in light absorption is relatively large between 750 and 850 nm. Furthermore, the absorptivity of light changes relatively with the state of the hemoglobin (oxygen saturation), and hence there is a possibility of being able to measure functional changes in the living organism by exploiting this change.

The photoacoustic wave measurement unit 203 measures (receives) a photoacoustic wave from the object and controls recording of a photoacoustic signal from the photoacoustic wave thus measured. An acoustic sensor provided in the photoacoustic wave measurement unit 203 employs a transducer element based on piezoelectric ceramic (PZT) or a transducer element of an electrostatic capacitance type, as used generally in an ultrasound diagnostic apparatus, or the like (below, the sensor which measures the photoacoustic wave is described simply as a "probe".) The details of the photoacoustic wave measurement unit are described below.

A scanning control unit 204 two-dimensionally controls the irradiation position of the measurement light and the position of the probe which measures the photoacoustic wave. During scanning, the irradiation position of the measurement light and the probe are driven simultaneously and controlled in such a manner that the optical axis of the measurement light coincides with the center of the probe. By capturing images while the scanning control unit 204 performs scanning of the measurement light and the probe in a two-dimensional fashion with respect to the object, it is possible to obtain a broad measurement range with a small probe. By this means, it is possible to measure the whole breast in diagnosis carried out in a breast clinic, for example.

The signal processing unit 205 carries out correction processing on the photoacoustic data measured by the photoacoustic wave measurement unit 203. The signal processing unit 205 carries out integration processing for noise reduction, and other correction processing. By repeatedly carrying out measurement at the same measurement position and then integrating the results, it is possible to reduce white noise, and to improve the S/N ratio of the photoacoustic data.

The holding unit 207 is a mechanism for holding an object. It is possible to adjust the thickness of the object to a thickness suited to the capture of photoacoustic diagnostic images, in accordance with the penetration depth of the measurement light. The holding unit 207 comprises a holding member which holds an object from either side, and a mechanism for altering the interval and pressure at which the object is held by the holding member.

The I/F 206 of the PAT 201 forms transmission means for transmitting photoacoustic data to the image processing unit 103. The I/F 206, together with the I/F 211 of the image processing unit 103, functions as an interface for performing data communications between the PAT 201 and the image processing unit 103. Desirably, the interfaces employ a communication standard which ensures communications in real time, and enables communication of large data volumes. The data communication method may be a wired method (for example, USB, IEEE 1394, HDMI (registered trademark), optical transmission, or the like), or a wireless method (for example, UWB (Ultra Wide Band), wireless LAN, millimeter-wave communications, and the like).

Next, the respective portions which make up the image processing unit 103 will be described.

The I/F 211 of the image processing unit is an interface on the image processing unit side. The I/F 211 has a similar function to the I/F 206 in the PAT 201, and exchanges data in coordination with the I/F 206.

The image constructing unit 212 generates photoacoustic diagnostic image data from measurement information of the object included in the received photoacoustic data. The image constructing unit 212 also constructs image information that is more desirable for diagnosis by applying correction processing of various kinds, such as brightness adjustment, distortion adjustment, target region extraction, and the like, to the obtained photoacoustic diagnostic image data.

The display unit 213 displays the photoacoustic diagnostic image constructed by the image constructing unit 212.

By means of a PAT system having the composition described above, it is possible to capture and display a photoacoustic diagnostic image of the object.

Figure 3:
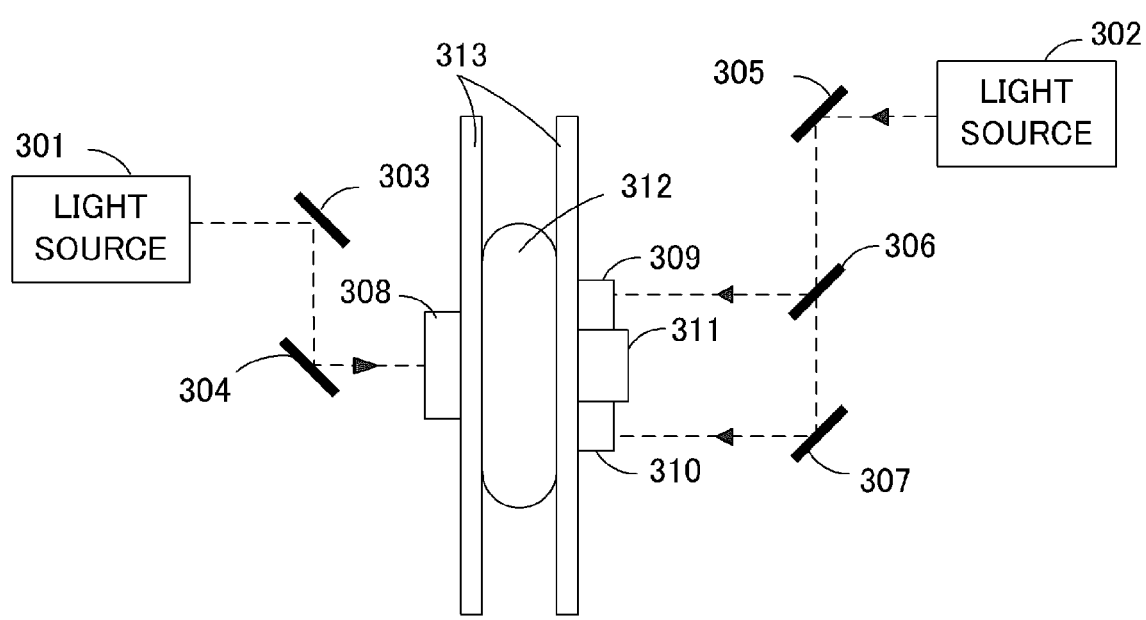
FIG. 3 is a conceptual diagram showing one example of the internal apparatus composition of a PAT according to the first embodiment.

FIG. 3 is a conceptual diagram showing one example of the internal apparatus composition of a PAT 201 according to a first embodiment of the invention.

In the PAT 201 according to the present embodiment, the measurement depth is improved by irradiating measurement light from either side of the object, as well as making it possible to obtain a high-quality photoacoustic diagnostic image with high contrast.

The light source 301 and the light source 302 are laser light sources which emit pulse light (having a pulse width of 10 nsec) in the near-infrared region having a central wavelength set between 530 and 1300 nm. The light source 301 generates measurement light which is irradiated onto an object 312 from a side opposite to the probe 311, and the light source 302 generates measurement light which is irradiated onto an object 312 from the same side as the probe 311. In the present embodiment, a construction is adopted in which different light sources are used for the measurement light on the probe side and the side opposite to the probe, but it is also possible to adopt a construction in which light from a single light source is split into two light beams. Furthermore, it is also possible to provide a plurality of light sources having different wavelengths.

The optical systems 303, 304, 305, 306, 307 guide the measurement light from the light source 301 and the light source 302, to the object 312.

The optical system 308 adjusts, for instance, enlarges, the measurement light on the side opposite to the probe, which is guided from the light source 301 via the optical systems (303 and 304). The optical systems 309 and 310 adjust, for instance, enlarge, the measurement light on the probe side which is guided from the light source 302 via the optical systems (305, 306, 307), and also deliver the measurement light obliquely to the object 312. The optical systems 309 and 310 are disposed on either side of the probe 311, and respectively diffract the measurement light in the direction of the probe.

The probe 311 which is composed by an alignment of a plurality of transducer elements receives a photoacoustic wave generated inside the object and converts the wave to an electrical signal (hereinafter, called "photoacoustic wave signal").

The object 312 is an object of measurement in the present embodiment. In the case of diagnosis in a breast clinic, the object is a breast.

The holding member 313 is a member, such as a flat plate, which holds the object 312. The holding member 313 on the probe side is desirably a member suited to propagation of a photoacoustic wave, as well as being transparent with respect to near-infrared light, since it forms one portion of the irradiation optical system. In general, a holding member made of polymethyl pentene, or the like, which is used in ultrasound diagnostic apparatuses is used as the holding member.

By means of the composition described above, it is possible to measure a photoacoustic wave by irradiation of measurement light from both the probe side and the side opposite to the probe, and to capture a photoacoustic wave diagnostic image by two-dimensional scanning.

Figure 4:
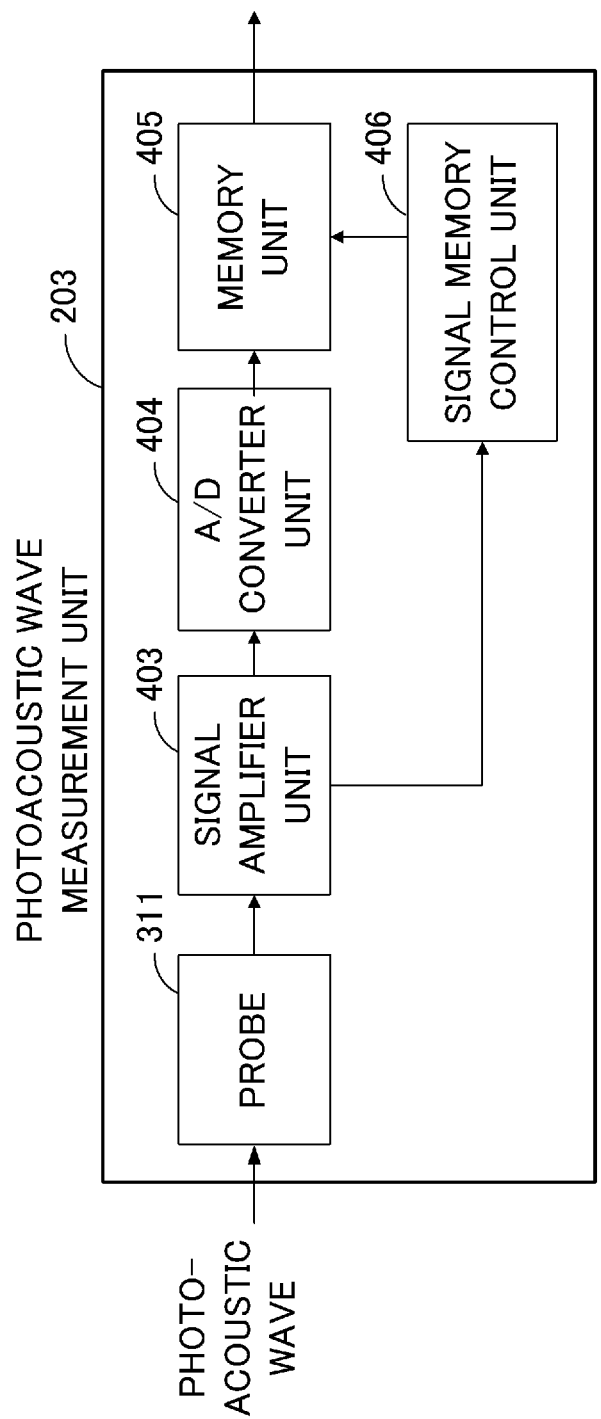
FIG. 4 is a functional block diagram of the photoacoustic wave measurement unit according to the first embodiment.

FIG. 4 is a functional block diagram of a photoacoustic wave measurement unit 203 in a first embodiment which describes the characteristics of the present invention.

The photoacoustic wave measurement unit 203 in the first embodiment comprises a probe 311 which receives a photoacoustic wave and converts the wave into an electrical signal and a signal amplifier unit 403 which amplifies a signal output by the probe 311. The photoacoustic wave measurement unit also comprises an A/D converter unit 404 which converts the wave to a digital signal, a memory unit 405 which records a signal that has been A/D converted, and a signal memory control unit 406 which controls a recording operation of the signal memory unit 405.

The signal amplifier unit 403 amplifies a very faint photoacoustic wave signal which is output by the probe 311. The signal amplifier unit 403 uniformly amplifies a photoacoustic wave signal in accordance with a previously established rate of amplification, and inputs a signal of a specific transducer element, of the transducer elements constituting the probe 311, to the signal memory control unit 406. Furthermore, the signal amplifier unit 403 also implements control (time gain control, hereinafter "TGC") for increasing or reducing the amplification gain for a photoacoustic wave from a position which is deep (i.e., relatively far from the surface of the object), in order to obtain diagnostic image data having uniform contrast, regardless of the measurement depth.

In order to calculate the density distribution of the light absorbing material inside the object from the measured photoacoustic wave signal, it is necessary to calculate the light energy actually irradiated onto the liquid absorbing material which has generated the photoacoustic wave. However, since the measurement light irradiated onto the object (and in particular, a living organism) penetrates into the deep parts of the object while diffusing and being attenuated to a large degree, it is not possible readily to estimate the light energy of the measurement light actually irradiated onto the light absorbing substrate, from the measured photoacoustic wave signal. Even with bodies of light absorbing materials of the same size, shape and absorption coefficient, the photoacoustic wave generated becomes weaker, the deeper the position inside the object, and it is not possible to perform measurement with the same contrast, directly and without modification. Therefore, TGC control should be implemented.

The A/D converter unit 404 converts the photoacoustic wave signals of all of the transducer elements of the probe, which is TGC controlled by the signal amplifier unit 403, from an analog signal to a digital signal. The digital signals output by the A/D converter unit 404 are input to the signal memory unit 405.

The memory unit 405 records the photoacoustic wave signals input from the A/D converter unit 404 on a recording medium (not illustrated). The memory unit 405 performs a recording operation in accordance with a command from the signal memory control unit 406. The group of signals required to generate diagnostic image data, which are recorded by the memory unit 405, are synthesized and specified as photoacoustic data.

The signal memory control unit 406 orders the start and halt of a recording operation to the memory unit 405. The signal level of the photoacoustic wave signal input from the signal amplifier unit 403 is checked and a command to start or halt a recording operation is issued to the memory unit 405 on the basis of this signal level. The details of this processing are described below.

In the present embodiment, the signal input to the signal memory control unit 406 is the output signal from the signal amplifier unit 403, but it is also possible to use a digital signal output by the A/D converter unit 404 or an output signal from the probe 311. Furthermore, by providing an envelope detector unit before the signal memory control unit 406 and inputting an envelope signal of the obtained photoacoustic signal to the signal control unit 406, it is also possible to achieve stable control independently of spontaneously occurring noise.

By means of the composition described above, it is possible to control recording of a photoacoustic signal in synchronism with irradiation of measurement light, on the basis of the actual photoacoustic signal which is measured.

Figure 5A:
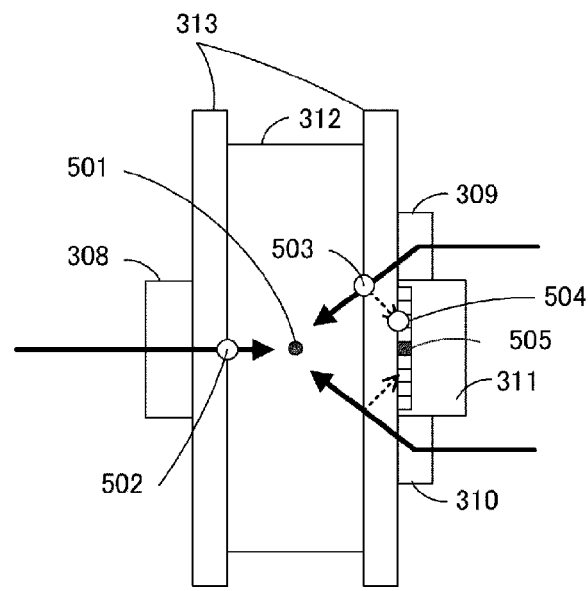
FIGS. 5A to 5C are conceptual diagrams for describing control of recording of a photoacoustic wave signal according to the first embodiment.
Figure 5B:
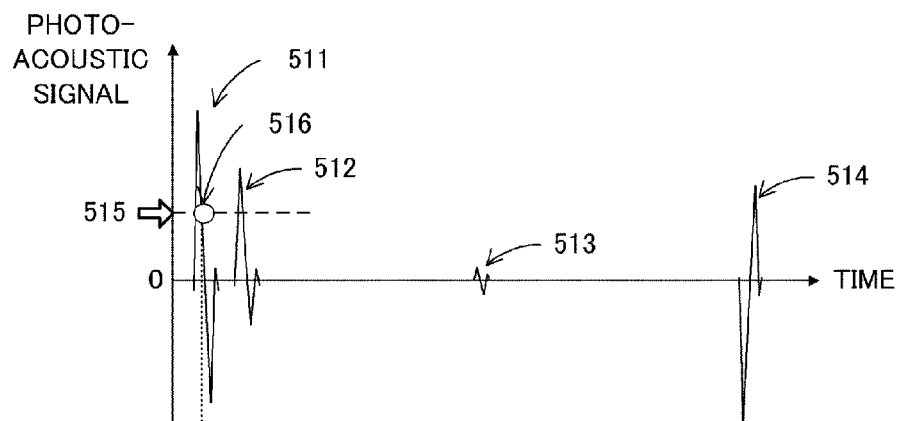
Figure 5C:
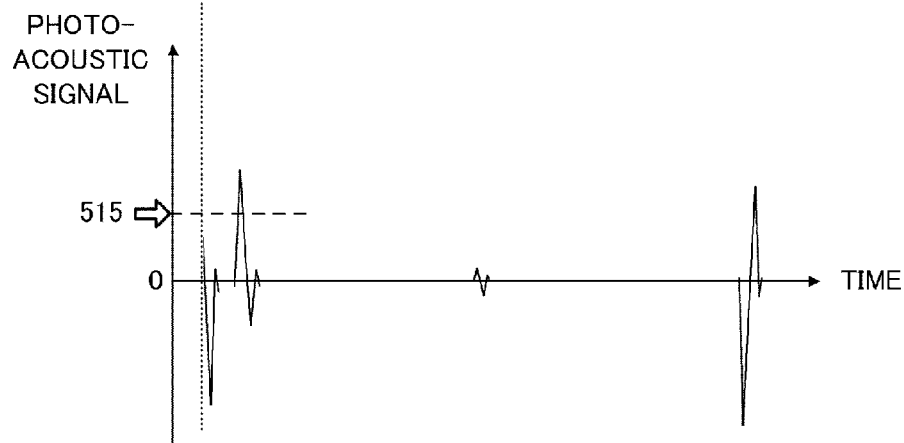

FIGS. 5A to 5C are conceptual diagrams for describing control of recording of a photoacoustic wave signal in the first embodiment which describes the characteristics of the present invention. FIG. 5A is a conceptual diagram showing a photoacoustic wave measurement method, FIG. 5B is a conceptual diagram showing one example of a recording control method for a photoacoustic wave signal which is measured, and FIG. 5C is a conceptual diagram showing a photoacoustic wave signal which is recorded.

The light absorbing material 501 is tissue located inside the object, which emits a photoacoustic wave by absorbing measurement light. In diagnosis in a breast clinic, new blood vessels caused by breast cancer produce an increase in blood flow and have higher light absorption than normal tissue, and therefore absorb energy of the measurement light (pulse light) and produce thermal expansion, resulting in the generation of a photoacoustic wave.

The interfaces 502, 503, 504 indicate locations having large signal characteristics apart from the light absorbing material which is the object of measurement, when photoacoustic waves are detected by a probe having a limited detection frequency band. The photoacoustic waves generated from these interfaces can be regarded as acoustic waves which are generated from portions other than the light absorbing material (and this term, "portions other than the light absorbing material", will be used herein as a convenient way to refer to such sources of acoustic waves that do not originate in the region of tissue being examined).

The interfaces 502 and 503 indicate interfaces between the object 312 and the holding member 313. The surface of the object is composed of normal tissue having a relatively low light absorptivity, but if measurement light is input while maintaining high light energy, then the photoacoustic wave generated by the surface of the object becomes large in size. Therefore, a large photoacoustic wave signal is detected at the interface between the object 312 and the holding member 313.

The interface 504 is the surface of the probe 311. In general, an acoustic matching member is provided in a portion of the surface of the probe in order to improve the detection efficiency of the photoacoustic wave. The acoustic matching member has light absorptivity in respect of the measurement light, and therefore the surface of the probe becomes a sound source for a photoacoustic wave. Even when the surface of the probe is protected with a reflective film, since the reflective film itself has a light absorptivity of several % (for example, about 3% in the case of gold), then it produces a large photoacoustic wave upon receiving measurement light which maintains a high light energy. The interface 504 is detected as a photoacoustic wave signal due to light which is reflected at the interface between the holding member 313 and the object 312 and arrives at the probe 311, of the measurement light on the probe side which is incident obliquely with respect to the holding member 313.

Apart from this, there are also cases where the holding member 313 forms a sound source, depending on the light absorption characteristics of the holding member 313. However, since a member which is transparent with respect to near-infrared light is generally used for the holding member, then the intensity of the photoacoustic wave from the holding member is much smaller than those from the interfaces 502, 503 and 504. Therefore, this photoacoustic wave is omitted from this description.

As described above, apart from the light absorbing material inside the object, which is the measurement object, there are also interfaces which have large signal characteristics. Photoacoustic waves are generated from these portions.

The recording of a photoacoustic wave signal in the first embodiment is controlled by using the photoacoustic wave signal received by one transducer element 505 which is disposed in the center of the probe 311.

The application of the present invention is not limited to a photoacoustic wave signal from a particular transducer element 505, and may use a signal of a transducer element at the probe tip; alternatively, any transducer element, such as a transducer element in the forward scanning direction, or a transducer element on the opposite side, or the like, may be selected.

FIG. 5B shows a conceptual diagram of photoacoustic wave signal characteristics measured by the transducer element 505. The vertical axis indicates the signal level of the photoacoustic wave signal detected by the probe 311 and the horizontal axis indicates time.

Signal 511 indicates a photoacoustic wave signal produced by the interface 504. In the measurement method according to the present embodiment, this is the first signal detected after the start of photoacoustic wave detection.

Signal 512 indicates a photoacoustic wave signal produced by the interface 503. In the method of measurement according to the present embodiment, this is the second signal which is detected.

The signal 513 is a photoacoustic wave signal from a light absorbing material 501 (corresponding to breast cancer) inside an object, which is the measurement object in photoacoustic diagnosis. In the measurement method according to the present embodiment, this is the third signal measured.

The signal 514 measured last is the photoacoustic signal produced by the interface 502.

The detection times of the signals 511, 512 and 514 are determined by the apparatus composition (the thickness and acoustic characteristics of the holding member 313) and the signal intensity is determined by the light absorptivity of the probe surface and the object 312, and therefore these signals are detected with the same signal characteristics, without any variation, in each measurement operation.

The detection timing of the signal 514 varies due to factors such as the holding interval and the acoustic characteristics of the object, but does not show great variation in relation to other signals in each measurement operation, and hence there is no disparity in characteristics, such as the large signal which is detected last during measurement.

As described above, it can be seen that the photoacoustic wave signal which is measured includes signal characteristics produced at interfaces determined by the apparatus composition.

Numeral 515 is a threshold value which is previously determined in order to control signal recording of the acoustic signal measured by the transducer element 505. The threshold value 515 according to the present embodiment is set on the basis of the peak value of the photoacoustic signal 511 produced by the interface 504. In order to determine the threshold level 515, it is necessary to identify the peak value of the signal 511 experimentally, but since the signal is a photoacoustic wave signal determined by factors depending on the apparatus construction, as described above, then this value should be measured in advance before diagnosis. In the PAT 201 according to the present embodiment which is capable of two-dimensional scanning of the measurement position of the photoacoustic wave, the prescribed threshold level 515 may be determined at all of the scanning positions or several representative positions.

When the photoacoustic wave reaches the transducer element 505, the transducer element 505 converts the received photoacoustic wave into an electrical signal. In the present embodiment, the signal memory control unit 406 instructs the memory unit 405 to start a recording operation, taking, as a trigger 516, the fact that the signal level of the transducer element 505 to which the wave is input has surpassed the threshold value level 515 once and then fallen below the threshold value 515. Thereafter, the memory unit 405 records the photoacoustic wave signal until reaching a number of samples required for photoacoustic diagnosis.

In the present embodiment, a two-value comparison such as that described above is used as a recording start trigger, but the application of the present invention is not limited to this. For example, if the speed of sound and the holding interval of the holding member and object are already known or can be estimated, then the detection times of the photoacoustic wave signals produced by the interfaces can be estimated by calculation, and therefore the actual appearance of a signal at the prescribed detection time can be taken as a trigger. Apart from this, the conditions and method of determining the trigger can be based on any desired method.

According to the recording control for the photoacoustic wave signal according to the present embodiment, the recorded photoacoustic signal is as shown in FIG. 5C.

As described above, the photoacoustic wave signal 511 produced by the interface 504 is measured first, and by utilizing the fact that it has large signal characteristics and setting desired trigger conditions, the recording of the photoacoustic wave signal can be controlled on the basis of the measured photoacoustic wave signal itself.

In the present embodiment, recording is controlled on the basis of a photoacoustic wave signal produced by the surface of the probe, but alternatively, it is also possible to perform the same control by using, as a trigger, a photoacoustic wave signal 512 produced by the interface between the object 312 and the holding member 313 which has the same characteristics in terms of the detection time and signal intensity.

Figure 6:
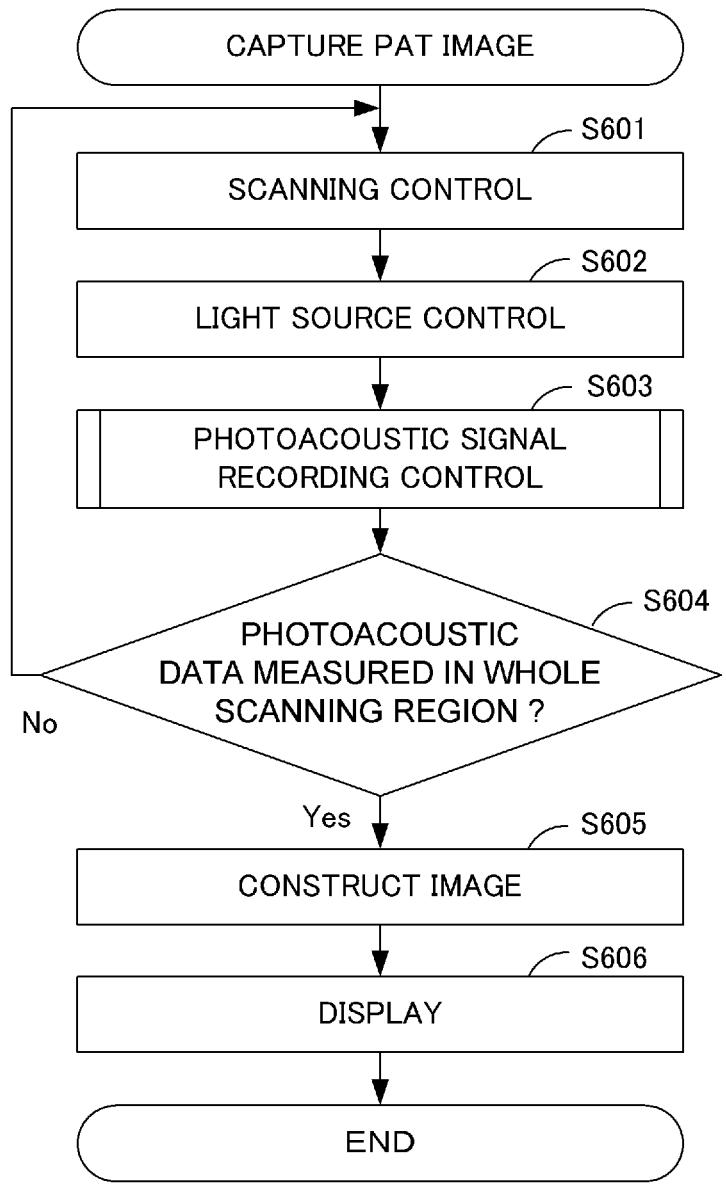
FIG. 6 is a flowchart showing the whole process according to the first embodiment.

FIG. 6 is a principal flowchart showing the whole flow of a photoacoustic diagnostic image capturing process according to a first embodiment of the invention.

In step S601, the scanning control unit 204 performs scanning control to drive the irradiation position of the measurement light and the position of the probe to the next measurement position.

At step S602, the irradiation unit 202 performs light emission control of the light sources 301 and 302, to emit near-infrared pulse laser light, which forms measurement light, toward the object.

In step S603, the signal memory control unit 406 controls recording of the photoacoustic wave signal in accordance with the first embodiment. The recording of the photoacoustic wave signal is controlled by using the actual photoacoustic wave which is measured. The details of this processing are described below.

At step S604, it is judged whether or not photoacoustic data has been measured for the whole scanning range. If measurement of photoacoustic data has been completed in the whole range, then the procedure advances to step S605. If this is not the case, then the procedure transfers to step S601 and repeats a measurement process.

At step S605, the image constructing unit 212 generates diagnostic image data from the photoacoustic data obtained by the processing to this point. Furthermore, image data or information which is more desirable for diagnosis is arranged by applying various correction processes, such as brightness adjustment, target region extraction, target site identification display, and the like, to the photoacoustic diagnostic image data thus obtained. Commonly known procedures may be employed for these image composition processes.

In step S606, the display unit 213 presents the photoacoustic diagnostic image constructed at step S605 to the user (for example, a doctor), and the sequence of processing for capturing a photoacoustic diagnostic image is terminated.

By means of the processing described above, it is possible to obtain a photoacoustic diagnostic image suitable for diagnosis, in photoacoustic measurement in which the measurement position can be scanned.

Figure 7:
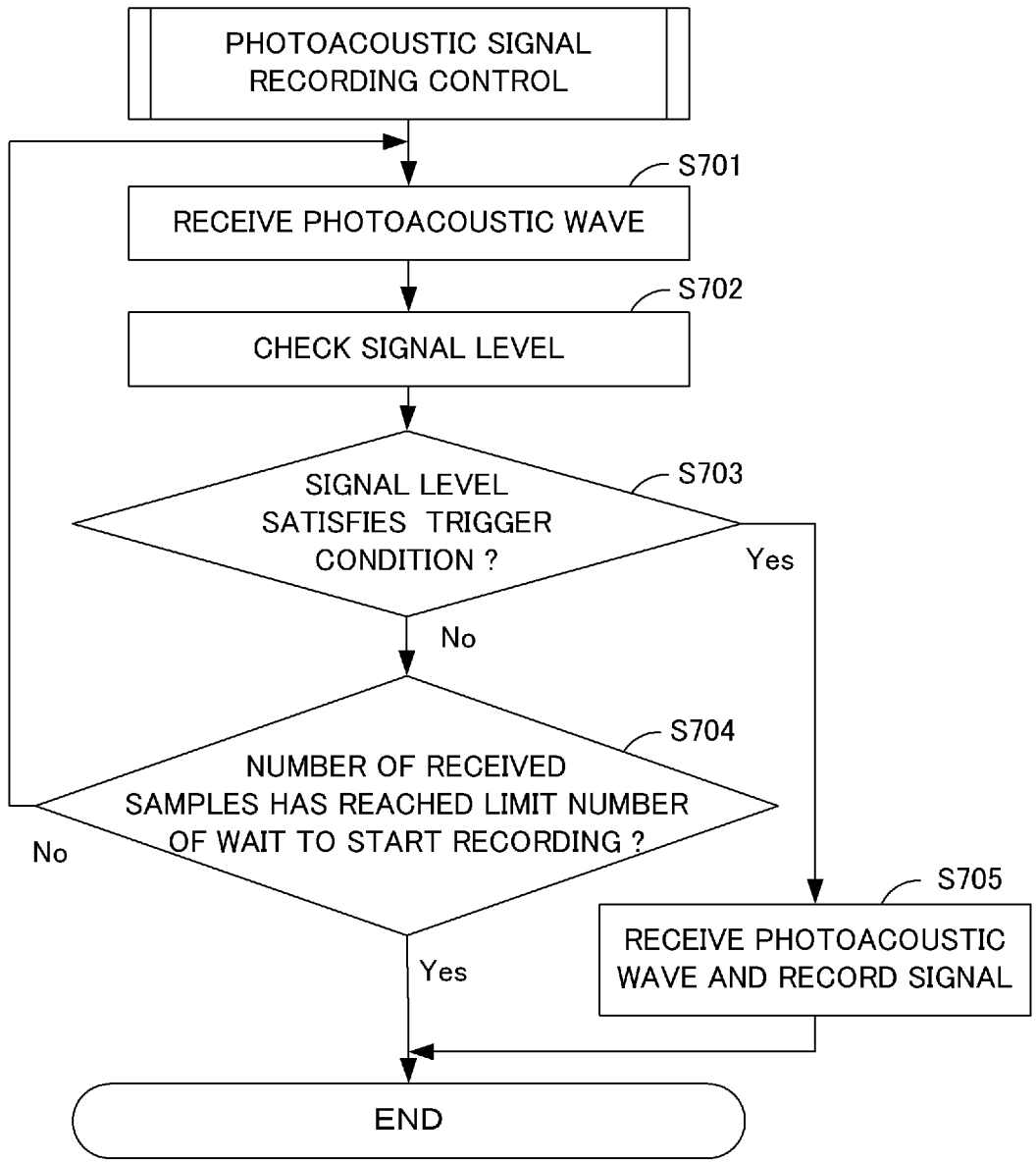
FIG. 7 is a flowchart of control of recording of a photoacoustic wave signal according to the first embodiment.

FIG. 7 is a flowchart for illustrating a flow of control of photoacoustic wave signal recording in the first embodiment which describes the characteristics of the present invention. The sequence of processing in this flowchart has the object of controlling the recording of a photoacoustic wave signal which is to be measured, by using the actual photoacoustic wave signal itself, as shown in FIG. 6. This processing explains the details of a portion of step S603 in FIG. 6.

At step S701, the probe 311 receives a photoacoustic wave produced as a result of irradiation of the measurement light at step S602, and converts the photoacoustic wave to a photoacoustic wave signal. Furthermore, the signal amplifier unit 403 inputs the signal from the transducer element 505 to the signal memory control unit 406.

At step S702, the signal memory control unit 406 checks whether or not the signal level of the transducer element 505 satisfies the trigger conditions.

At step S703, the signal memory control unit 406 judges whether or not the signal level confirmed in step S702 has satisfied the trigger condition 516 in respect of the previously established threshold level 515. If the signal level has satisfied the condition, processing transfers to step S705. If this is not the case, processing transfers to step S704.

At step S704, the signal memory control unit 406 judges whether or not the number of received samples of a photoacoustic wave signal has reached a previously established limit for waiting to start recording. If the number of samples has reached the limit, then the sequence of recording control processing for the photoacoustic signal is terminated, without recording a photoacoustic wave signal. If this is not the case, then processing transfers to step S701 to wait for the next signal.

In step S705, the signal memory control unit 406 instructs the start of a recording operation to the memory unit 405. The signal memory unit 405 having received this command then receives a number of photoacoustic wave signals corresponding to the number of samples required for photoacoustic diagnosis, records the signals as photoacoustic data in a memory, and then terminates the sequence of recording control processing for photoacoustic wave signals.

By means of the processing described above, it is possible to control recording of photoacoustic wave signals in accordance with the first embodiment.

According to the present embodiment, in a PAT system which irradiates measurement light onto an object from both the side opposite to the probe and the probe side, while holding the object by means of a holding member, it is possible to control recording of photoacoustic wave signals in synchronism with the irradiation of measurement light, without providing an optical system for detecting measurement light. The recording of photoacoustic wave signals can be controlled by using a photoacoustic wave signal which is produced at the interface between the holding member and the probe by measurement light from the probe side. By this means, it is possible to omit the portion of the optical composition for detecting measurement light in order to control recording of photoacoustic wave signals, and therefore costs can be reduced. More specifically, it is possible to achieve detection of the irradiation timing by means of a simple composition.

Moreover, detecting the measurement light has required the use of a portion of the measurement light by splitting the measurement light by an optical system, such as a half mirror, or the like, but it is possible to replace this with a general mirror, and the use efficiency of the measurement light can be improved, as well as lower costs.

Second Embodiment

A second embodiment of the present invention is now described with reference to the drawings.

In the first embodiment, recording control of the photoacoustic wave signals is carried out on the basis of a large photoacoustic wave which is produced by the measurement light on the probe side, assuming a composition which irradiates measurement light from both sides of the object.

On the other hand, if the penetration depth of the measurement light is sufficiently large with respect to the thickness of the object, there is no need to irradiate measurement light from both sides of the object, and hence photoacoustic measurement is possible with a simpler apparatus composition using measurement light in one direction, from the side opposite to the probe only.

The characteristic feature of the second embodiment is that recording of photoacoustic wave signals is controlled by applying the present invention to an apparatus composition where photoacoustic measurement is carried out only using measurement light from the side opposite to the probe.

The description of the present embodiment is centered on the characteristic described above.

The PAT system in the present embodiment can be achieved by means of a composition similar to the functional block (FIG. 2) according to the first embodiment and the photoacoustic wave measurement unit can be achieved by means of a composition similar to the functional block (FIG. 4) according to the first embodiment, and therefore description thereof is omitted here.

Furthermore, the whole flow of the photoacoustic diagnostic imaging process according to the present embodiment is the same as the flowchart in FIG. 6 according to the first embodiment, and description thereof is omitted here.

Figure 8A:
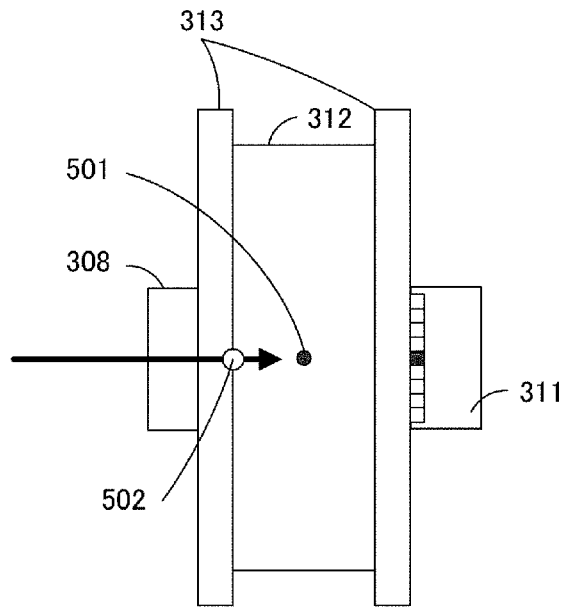
FIGS. 8A to 8C are conceptual diagrams for describing control of recording of a photoacoustic wave signal according to a second embodiment.
Figure 8B:
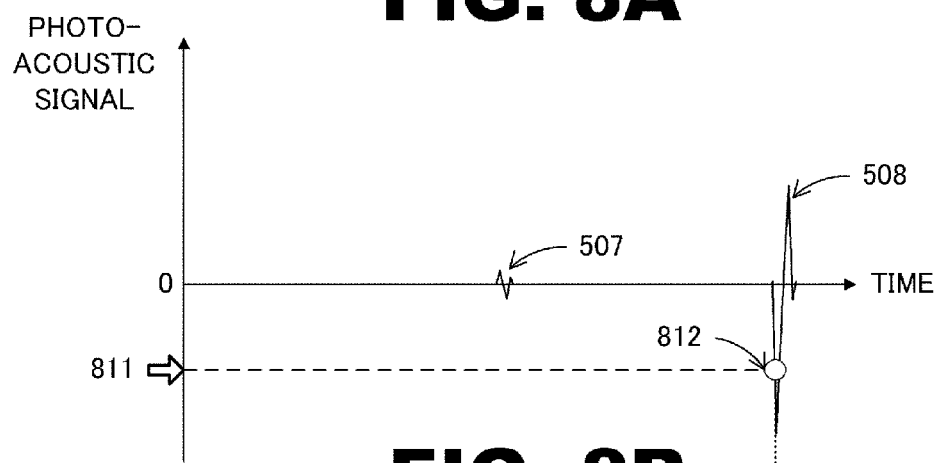
Figure 8C:
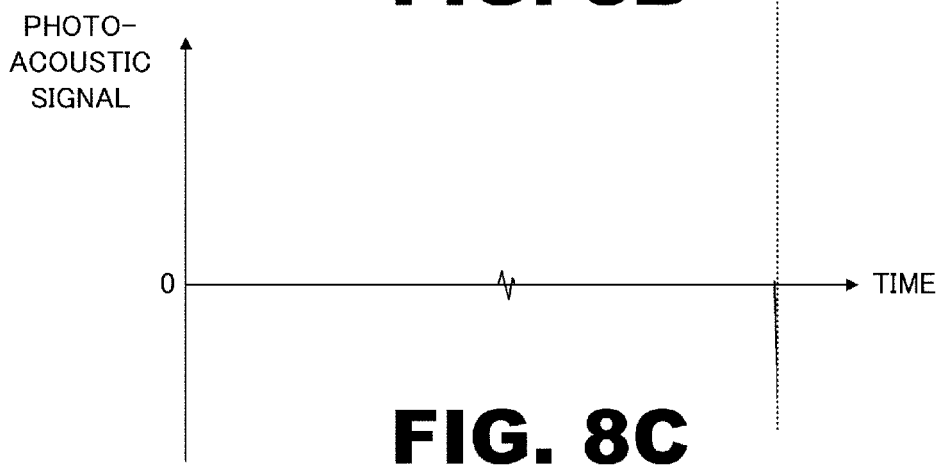

FIGS. 8A to 8C are conceptual diagrams for describing control of photoacoustic wave signal recording in the second embodiment which describes the characteristics of the present invention. FIG. 8A is a conceptual diagram showing a photoacoustic wave measurement method, FIG. 8B is a conceptual diagram showing one example of a recording control method for a measured photoacoustic wave signal, and FIG. 8C is a conceptual diagram showing a recorded photoacoustic wave signal.

In the photoacoustic wave diagnosis according to the present embodiment, since the object is irradiated with no measurement light from the probe side, there are no signals due to the interface between the holding member 313 and the probe 311, or the interface between the object 312 and the holding member 313. Consequently, compared to the photoacoustic wave signal of the first embodiment, a large signal is not measured immediately after the start of measurement. Signal 508 is a photoacoustic signal produced by the object surface 502 on the side opposite to the probe.

811 is a threshold value at which recording of the photoacoustic wave signals is ended. The threshold value 811 according to the present embodiment is set on the basis of the peak value of signal 508 and the magnitude of the signal of the light absorbing material 501, which is the measurement object. The threshold value 811 must be set to a position greater than the photoacoustic wave signal 507 of the light absorbing material 501 which is effective for photoacoustic diagnosis and smaller than the photoacoustic wave signal 508 of the interface 502.

The signal memory control unit 406 instructs the memory unit 405 to start a recording operation, simultaneously with the irradiation of measurement light. When the signal from the signal amplifier unit 403 exceeds the threshold level 811, the signal memory control unit 406 takes this point in time as a trigger 812 to halt recording, and instructs the memory unit 405 to halt a recording operation. The photoacoustic wave signal recorded thus far by the memory unit 405 is taken as photoacoustic data to be used for photoacoustic diagnosis.

Figure 9:
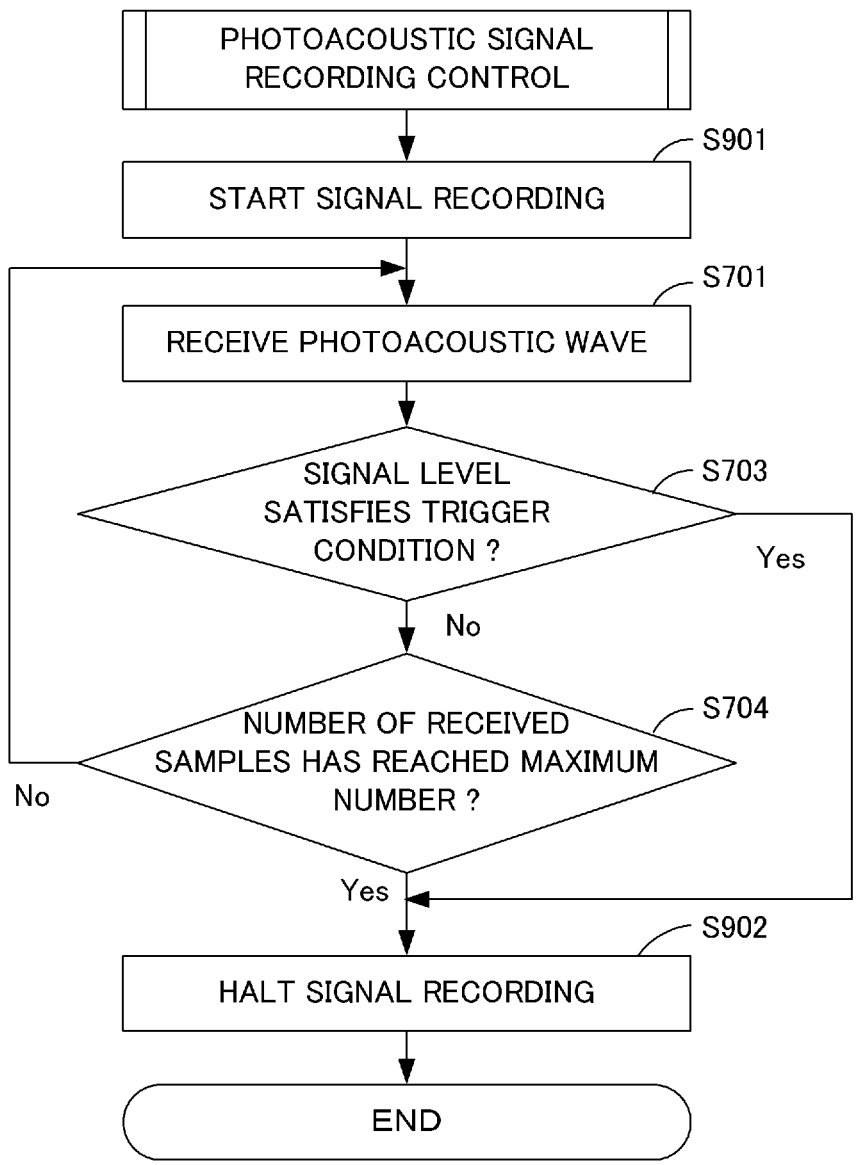
FIG. 9 is a flowchart of control of recording of a photoacoustic wave signal according to the second embodiment.

FIG. 9 is a flowchart for illustrating a flow of photoacoustic signal recording control processing in the second embodiment which describes the characteristics of the present invention. The sequence of processing in the present flowchart has the object of implementing the same control by extracting a post trigger for controlling recording of photoacoustic wave signals, on the basis of the characteristics of a photoacoustic wave signal which is measured by measurement light on the side opposite to the probe only.

Compared to the flowchart in FIG. 7 according to the first embodiment, this second embodiment additionally comprises a signal recording start step S901 and a signal recording halt step S902.

At step S901, the signal memory control unit 406 instructs the signal memory unit 405 to start a photoacoustic wave signal recording operation, similarly to the light source control in step S602. More specifically, the signal memory control unit 406 instructs the start of a recording operation when the light source emits light (in other words, when light is irradiated onto the object). The memory unit 405 which has received this command records the photoacoustic wave signal from this point in time.

In step S902, the signal memory control unit 406 instructs the memory unit 405 to halt a recording operation of the photoacoustic signal. The memory unit 405 which has received this command halts the recording of the photoacoustic wave signal up to this point in time.

By means of the processing thus far, it is judged whether the signal level has exceeded the threshold level by comparing the photoacoustic wave signal with a threshold level for controlling recording of the photoacoustic wave signal. Taking this as a post trigger, data recorded by the memory unit 405 up to this time is taken as valid photoacoustic data.

If the trigger conditions have not been satisfied for all of the received samples, then the data recorded to that point may be invalidated.

By means of the processing described above, it is possible to control recording of photoacoustic wave signals in accordance with the second embodiment.

According to the present embodiment, even with an apparatus composition which performs photoacoustic diagnosis by means of measurement light from the side opposite to the probe only, without irradiating measurement light from the probe side, it is possible to control recording of photoacoustic wave signals by using the photoacoustic wave from the surface of the object on the side opposite to the probe.

Third Embodiment

A third embodiment of the present invention is now described with reference to the drawings.

In the first and second embodiments, recording of photoacoustic wave signals is controlled on the basis of a photoacoustic wave signal generated by a representative element, from among the plurality of transducer elements which constitute the probe.

The characteristic feature of the third embodiment is that recording of photoacoustic wave signals is controlled stably in respect of noise which becomes intermixed spontaneously into the signals generated by the individual transducer elements of the plurality of elements which constitute the probe, by applying calculation for summing the signals of a plurality of transducer elements.

The PAT system according to the present embodiment can be implemented by means of a similar composition to the functional block according to the first embodiment (FIG. 2), and therefore description thereof is omitted here.

Furthermore, the whole flow of the photoacoustic diagnostic imaging process according to the present embodiment is the same as the flowchart in FIG. 6 according to the first embodiment, and description thereof is omitted here.

Figure 10:
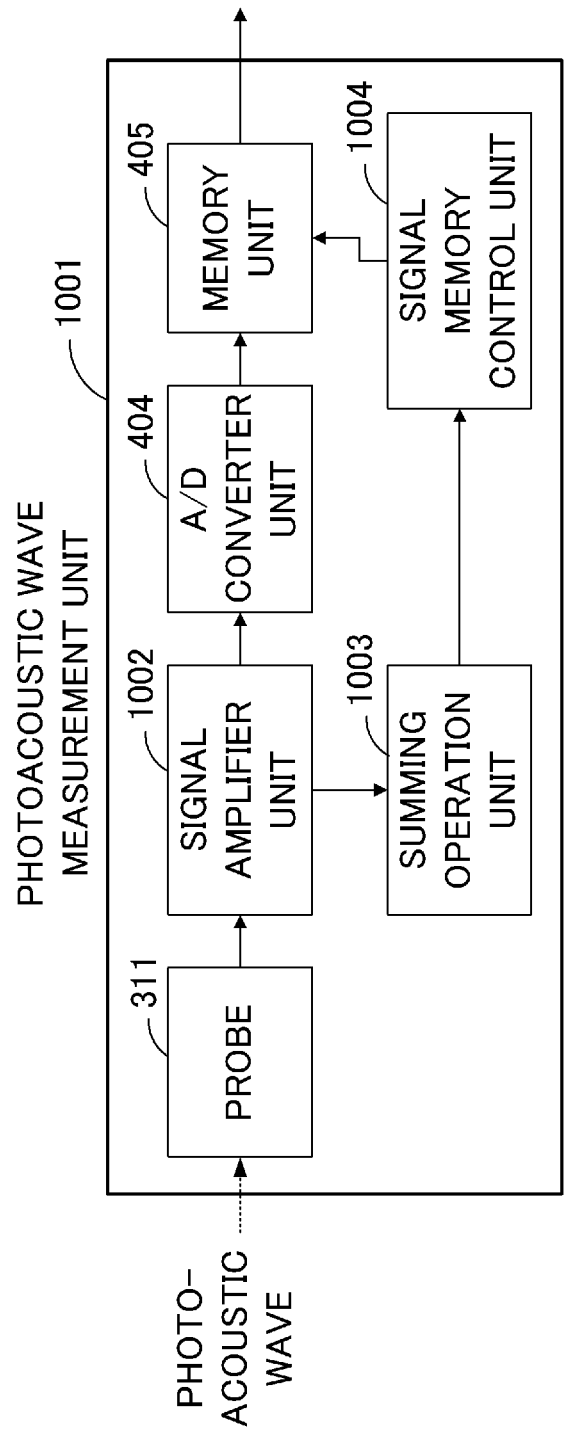
FIG. 10 is a functional block diagram of the photoacoustic wave measurement unit according to a third embodiment.

FIG. 10 is a functional block diagram of a photoacoustic wave measurement unit in a third embodiment which describes the characteristics of the present invention.

The photoacoustic wave measurement unit 1001 in the third embodiment is additionally provided with a summing operation unit 1003, compared to the photoacoustic wave measurement unit 203 in FIG. 2 according to the first embodiment.

The signal amplifier unit 1002 amplifies the very small photoacoustic wave signals generated by the plurality of transducer elements which constitute the probe 311. The signal amplifier unit 1002 outputs the signals of all of the transducer elements to the A/D conversion unit 504, as well as outputting the signals of all or a portion of the transducer elements (in other words, two or more transducer elements), to the summing operation unit 1003.

The summing operation unit 1003 sums the photoacoustic wave signals of all or a portion of the transducer elements of the plurality of transducer elements which constitute the probe 311, which are input from the signal amplifier unit 1002. By means of a summing process, signals from interfaces apart from the light absorbing material, which is the measurement object, are extracted. The summed signal is output to the signal memory control unit 1004. The details of this are described hereinafter.

The signal memory control unit 1004 instructs the memory unit 405 to start and halt a recording operation, on the basis of the summed signal input from the summing operation unit 1003.

By means of the photoacoustic wave measurement unit having the composition described above, even if spontaneous noise has become intermixed into the photoacoustic wave signals generated by the plurality of transducer elements which constitute the probe, it is possible to control recording of photoacoustic wave signals in a stable fashion.

Figure 11A:
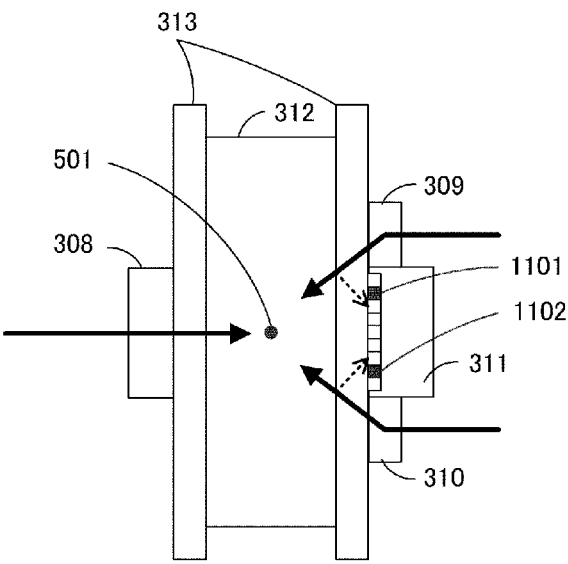
FIGS. 11A to 11D are conceptual diagrams for describing control of recording of a photoacoustic wave signal according to the third embodiment.
Figure 11B:
Figure 11C:
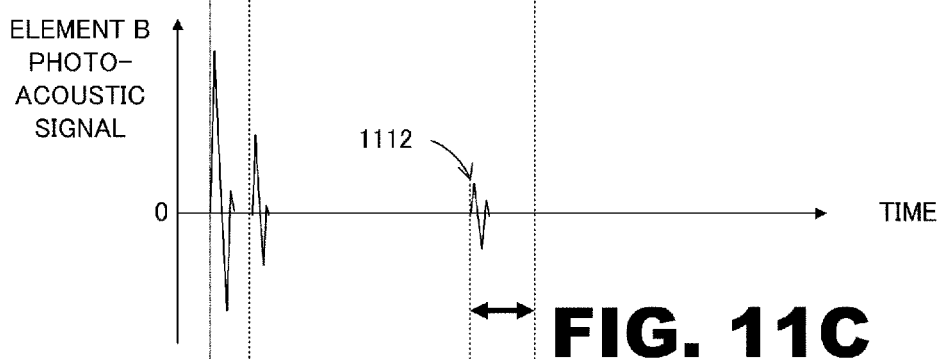
Figure 11D:

FIGS. 11A to 11D are conceptual diagrams for describing control of the recording of photoacoustic wave signals in the third embodiment which describes the characteristics of the present invention. FIG. 11A shows a measurement method, FIGS. 11B and 11C respectively show photoacoustic wave signals detected by the transducer elements 1101 and 1102, and FIG. 11D shows a signal calculated by summing the signals in FIG. 11B and FIG. 11C. In FIGS. 11B to 11D, the vertical axis represents the photoacoustic wave signal and the horizontal axis represents time.

The transducer elements 1101 and 1102 are transducer elements of probe 311. The transducer elements 1101 (element A) and 1102 (element B) have different positions, and hence a differential corresponding to their positional relationship occurs in their photoacoustic wave signals.

Comparing FIG. 11B and FIG. 11C, the detection time of a photoacoustic wave generated by the light absorbing material 501 inside the object 312 is different in the two transducer elements 1101 and 1102, as indicated by signal 1111 and signal 1112. This is because a spherical photoacoustic wave which is emitted by the light absorbing material 501 is detected at different distances.

As opposed to this, the times of the photoacoustic wave signals generated by the interface between the probe 311 and the holding member 313 and the interface between the object 312 and the holding member 313 coincide in the two transducer elements 1101 and 1102. This is because the distances to the interface between the probe 311 and the holding member 313 and the interface between the object 312 and the holding member 313 are uniform, and hence the planar wave-shaped photoacoustic wave is detected at the same distance.

If the photoacoustic wave signals detected by the transducer elements 1101 and 1102 are averaged, interface photoacoustic signals having the same detection timing are integrated, whereas the photoacoustic signal of the light absorbing material 501 which has a different detection timing is not integrated, and therefore the signal characteristics such as those in FIG. 11D are obtained. More specifically, as a result of the summing process, it is possible to extract the interface photoacoustic signals.

Furthermore, even if noise has become intermixed spontaneously into the photoacoustic wave signals generated by the individual transducer elements, it is possible to reduce the effects of noise by means of the summing process.

Here, for the purpose of simplicity, the photoacoustic wave signals of two transducer elements 1101 and 1102 are used, but in actual practice, it is possible to extract the interface photoacoustic signals with good accuracy, by using the signals from a greater number of elements.

From the foregoing, it is possible to reduce the effects of spontaneous noise and to achieve stable functioning, by utilizing the fact that the photoacoustic wave generated by the interface is a substantially planar-shaped sound wave, and by judging trigger conditions through extracting only the portion of the interface photoacoustic wave signal required to control signal recording.

Numeral 1121 indicates a threshold value which is previously determined in order to control signal recording of the signal summed by the summing operation unit 1003. The threshold value 1121 according to the present embodiment is set on the basis of the peak value of a first photoacoustic signal. Furthermore, the signal memory control unit 406 instructs the memory unit 405 to start a recording operation, taking, as a trigger, the fact that the input summed signal level once surpasses and then falls below the threshold value level 1121. From this trigger 1122, the memory unit 405 carries out recording of the photoacoustic wave signal until reaching a number of samples required for photoacoustic diagnosis.

According to the present embodiment, the fact that the photoacoustic waves generated by the interfaces included in the photoacoustic signal are planar waves is used in order to extract only the photoacoustic signal from an interface required to control signal recording, thereby making it possible to reduce the effects of spontaneous noise and to achieve stable functioning.

Fourth Embodiment

Furthermore, the object of the present invention can of course also be achieved as described below. In other words, a storage medium (or recording medium) which stores program code of software for achieving the functions of the respective embodiments described above is supplied to a system or apparatus. A computer (or CPU or MPU) in the system or apparatus then reads out and executes the program code stored on the storage medium. In this case, the actual program code read out from the storage medium achieves the functions of the embodiments described above, and the storage medium on which this program code is stored constitutes the present invention.

Furthermore, by executing the program code read out by the computer, an operating system (OS), or the like, which is running on the computer performs all or a portion of the actual processing, on the basis of instructions in the program code. Cases where the functions of the embodiments described above are achieved by this processing are of course also included in the present invention.

Moreover, the program code read out from the recording medium may be written to a memory provided in a functional expansion card inserted into a computer, or a functional expansion unit connected to a computer. The present invention of course also includes a case where a CPU provided in the functional expansion card or functional expansion unit, or the like, carries out all or a portion of actual processing on the basis of instructions in this program code, and where functions of the embodiments described above are achieved by this processing.

When the present invention is applied to the recording medium described above, program code corresponding to the flowchart described previously is stored on the recording medium.

Other Embodiments

When a new system is composed by suitably combining various technologies in the respective embodiments described above, the system formed by this combination also comes within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-169299, filed on Jul. 28, 2010, which is hereby incorporated by reference herein in its entirety.

The invention claimed is:

1. A photoacoustic diagnostic apparatus, comprising:
   a light source;
   a probe which receives an acoustic wave generated when an object is irradiated with light from said light source and which converts the acoustic wave into an electrical signal; and
   a computer, comprising memory and at least one of a CPU and an MPU, cooperating to function as a memory unit which is configured to record the electrical signal on a recording medium, and
   wherein said computer controls whether or not to cause said memory unit to record the electrical signal on the recording medium,
   wherein said computer controls whether or not to record the electrical signal on the basis of a timing at which said probe receives an acoustic wave which is generated from a portion other than a region of interest inside the object and is generated by light irradiation of the object from said light source.

2. The photoacoustic diagnostic apparatus according to claim 1, wherein said computer determines whether or not the acoustic wave received by said probe is an acoustic wave generated from the portion other than a region of interest, by comparing an intensity of an electrical signal converted from the acoustic wave received by said probe with a prescribed threshold value.

3. The photoacoustic diagnostic apparatus according to claim 2, wherein said computer determines that the acoustic wave received by said probe is an acoustic wave generated from the portion other than a region of interest, when the intensity of the electrical signal has exceeded the prescribed threshold value and subsequently fallen below the prescribed threshold value.

4. The photoacoustic diagnostic apparatus according to claim 2, wherein said computer determines that the acoustic wave received by said probe is an acoustic wave generated from the portion other than a region of interest, when the intensity of the electrical signal has exceeded the prescribed threshold.

5. The photoacoustic diagnostic apparatus according to claim 1, wherein
   the object is irradiated with light from said light source from at least a first side, which is the same side as a side toward which said probe is located relative to the object,
   the acoustic wave generated from the portion other than a region of interest is an acoustic wave generated from a surface of said probe when light from said light source reaches a surface of said probe, and
   said computer implements control to start recording of the electrical signal by said memory unit, when said probe has received an acoustic wave generated from said surface of said probe.

6. The photoacoustic diagnostic apparatus according to claim 1, wherein
   the object is irradiated with light from said light source from a first side that is opposite to a side toward which said probe is located relative to the object,
   the acoustic wave generated from the portion other than a light absorbing material is an acoustic wave generated from a surface of the object when the light from said light source reaches the surface of the object, and
   said computer implements control to start recording of the electrical signal by said memory unit when the object has been irradiated with light from said light source, and implements control to halt recording of the electrical signal when said probe has received the acoustic wave generated from the surface of the object.

7. The photoacoustic diagnostic apparatus according to claim 1, wherein
   said probe includes a plurality of elements, and a summing operation unit is provided to generate a summed signal by summing electrical signals converted by two or more of said elements, and
   said computer determines whether or not the received acoustic wave is an acoustic wave generated from the portion other than a region of interest, by comparing the intensity of the summed signal obtained by said summing operation unit with a prescribed threshold value.

* * * * *